United States Patent [19]
Kaufman et al.

[11] Patent Number: 5,517,021
[45] Date of Patent: *May 14, 1996

[54] APPARATUS AND METHOD FOR EYE TRACKING INTERFACE

[75] Inventors: Arie A. Kaufman, Plainview; Amit Bandopadhay, Smithtown, both of N.Y.; George J. Piligian, Englewood Cliffs, N.J.

[73] Assignee: The Research Foundation State University of New York, Albany, N.Y.

[ * ] Notice: The term of this patent shall not extend beyond the expiration date of Pat. No. 5,360,971.

[21] Appl. No.: 330,924

[22] Filed: Oct. 28, 1994

Related U.S. Application Data

[63] Continuation of Ser. No. 6,199, Jan. 19, 1993, Pat. No. 5,360,971.
[51] Int. Cl.$^6$ ...................................................... G01V 9/04
[52] U.S. Cl. ...................... 250/221; 340/825.19; 128/745
[58] Field of Search ..................................... 250/221, 216; 128/733, 745; 340/705, 706, 825.19, 980; 351/209, 210; 364/514, 516, 550

[56] References Cited

U.S. PATENT DOCUMENTS

| | | | |
|---|---|---|---|
| 5,293,187 | 3/1994 | Knapp et al. | 351/210 |
| 5,360,971 | 11/1994 | Kaufman et al. | 250/221 |

FOREIGN PATENT DOCUMENTS

| | | |
|---|---|---|
| 0301790 | 1/1989 | European Pat. Off. . |
| 0468340 | 1/1992 | European Pat. Off. . |
| 2170910 | 8/1986 | United Kingdom . |
| 2201069 | 8/1988 | United Kingdom . |
| WO8303191 | 9/1983 | WIPO . |
| WO9113584 | 9/1991 | WIPO . |

OTHER PUBLICATIONS

The Invention Of Memory, A View Of The Brain by Israel Rosenfield, 1988.
The Eye Wink Control Interface: Using the Computer To Provide The Severely Disabled With Increased Flexibility and Comfort, Shaw, et al., *Third Annual IEEE Symposium on Computer-Based Medical Systems*, Jun. 3-6, 1990, 105-111.
Bahill, A. T., *Bioengineering: Biomedical, Medical and Clinical Engineering*, Prentice Hall, Inc., Englewood Cliffs, New Jersey, 1981.
Neuman, M. R., Fleming, D. G., Cheung, P. W. and Ko, W. H., *Physical Sensors for Biomedical Applications*, CRC Press, Inc., Boca Raton, Florida, 1977.
Yamada, M., Fukuda, T. and Hirota, M., "A New Eye Movement Analyzer: Autocalibration and Wireless Transmission", *IEEE Medical and Biological Society Eleventh Annual International Conference*, 1989. pp. 861–863.
Robinson, D. A., Gordon, J. L. and Gordon, S. E., "A Model of the Smooth Pursuit Eye Movement System", *Biology Cybern*, 55 (1986), pp. 43–57.
Wall III, C. and Black, F. O., "Algorithms for the Clinical Analysis of Nystagmus Eye Movements", *IEEE Transactions on Biomedical Engineering*, BME/28, (September, 1981).

(List continued on next page.)

*Primary Examiner*—Edward P. Westin
*Assistant Examiner*—John R. Lee
*Attorney, Agent, or Firm*—Morgan & Finnegan

[57] ABSTRACT

An eye tracking interface system for generating communication and control functions as a result of pre-defined eye gestures is disclosed. The system includes a detecting device adapted to detect bio-electromagnetic signals generated by eye movements. A first processor receives the detected bio-electromagnetic signals, and generate tokens corresponding to said pre-defined eye gestures. A second processor receives the tokens, and generates command signals based on a protocol correlating tokens to desired command signals. Thereafter, a user interface responds to said command signals, and provides control functions in response to said command signals.

8 Claims, 7 Drawing Sheets

OTHER PUBLICATIONS

Zeevi, Y. Y., and Peli, E., "Smooth Eye–Movement Control With Secondary Visual Feedback", *Journal of the Optical Society of America. A, Optics and Image Science,* I, (June, 1984) pp. 628–634.

Bahill, A. J., Brockenbrough, A. E., and Troost, B. T., "Variability and Development of a Normative Data Base for Saccadic Eye Movements", *Invest. Opthalmol. Vis. Sci.,* 21, (Jul. 1981) p. 116–125.

Cohen, A., *Biomedical Signal Processing,* CRC Press, Inc., Boca Raton, Florida, 1986.

Inchingolo, P. and Spanio, M., "On the Identification and Analysis of Saccadic Eye Movements—A Quantitative Study of the Processing Procedures", *IEEE Transactions on Biomedical Engineering,* BME/32, Sep., 1985. pp. 683–694.

Yamada, M. and Fukuda, T., "Quantitative Evaluation of Eye Movements as Judged by Sight–Line Displacements", *SMPTE Journal,* 95, (Dec., 1986) pp. 1230–1241.

Ballard, D. H. and Brown, C. M., *Computer Vision,* Prentice Hall, Englewood Cliffs, New Jersey, 1982.

Juhola, M., Jäntti, V., Pyykkö, I., Magnusson, M., Schalén, L. and Åkesson, M., "Detection of Saccadic Eye Movements Using a Non–Recursive Adaptive Digital Filter", *Computer Methods and Programs in Biomedicine,* 21 (1985) pp. 81–88.

Giacalone, A. and Kaufman, A., "Tools for Interactive Prototyping of Two–Dimensional and Three–Dimensional User Interfaces", *Augmented Interactive Computer Capabilities,* (A. Klinger) Plenum Press, 1990.

Kaufman, A., "A Three–Dimensional User Interface", *NCGA, 1989 Tenth Annual Conference,* Philadelphia, Pennsylvania, April 1989, pp. 361–367.

Kaufman, A., Yagel, R. and Bakalash, R., "Direct Interaction with a 3D Volumetric Environment", *Proceedings 1990 Symposium on Interactive 3–D Graphics,* Snowbird, Utah, Mar., 1990, pp. 33–34.

Kaufman, A. and Yagel, R., "Tools for Interaction in Three Dimensions" *Work with Computers: Organizational Management, Stress and Health Aspects,* M. J. Smith and G. Salvendy (Eds.) Elsevier Science Publishers B.V., Amsterdam, The Netherlands, Sep., 1989, pp. 468–475.

Ishii, M., Sakane, S., Kakikura, M. and Mikami, Y. 1987. "A 3–D Sensor System for Teaching Robot Paths and Environments", *The International Journal of Robotics Research* 6(2), pp. 45–59.

Yin, B., "Using Vision Data in an Object–Level Robot Language–RAPT", *The International Journal of Robotics Research,* 6(1) pp. 43–58, 1987.

Harris, T. R. "Electronic Eye–Position Monitoring Interface", *Proceedings of the Eleventh Annual Northeast Bioengineering Conference,* (ed. W. Kukinski, W. Ohley, 1985) pp. 267–270.

Young, L. R., Sheena, D., "Methods and Designs, Survey of Eye Movement Recording Methods", *Behavioral Research Methods and Instructions,* 1975, vol. 7(5), pp. 397–429.

Behrens, F., Collewijn, H. and Grusser, O.–J., "Velocity Step Responses of the Human Gaze Pursuit System. Experiments with Sigma–Movement", *Vision Res.* 1985 25:pp. 893–905.

Kommerell, G. and Täumer, R., "Investigations of the Eye Tracking System Through Stabilized Retinal Images", *Cerebral Control of Eye Movements and Motion Perception,* J. Dichgans and E. Bizzi (Eds.) Karger, Basil, 1972.

Wyatt, H. J. and Pola, J., "The Role of Perceived Motion in Smooth Pursuit Eye Movements", *Vision Res.,* 19 (1979) pp. 613–618.

Young, L. R., "Pursuit Eye Tracking Movements", *The Control of Eye Movements* P. Back–Y–Rita, Y. Rita and C. C. Collins (Eds.), New York, 1971, pp. 429–443.

Bock, O., "Coordination of Arm and Eye Movements in Tracking of Sinusoidally Moving Targets", *Behavioral Brain Research,* 24 (1987) pp. 93–100.

APPARATUS AND METHOD FOR EYE TRACKING INTERFACE

This is a continuation of application Ser. No. 08/006,199, filed Jan. 19, 1993, now U.S. Pat. No. 5,360,971.

This invention relates to systems for utilizing eye movements for communication and control. More particularly, the invention relates to systems for detecting eye movements, deriving signals from such movements, processing those signals to generate signals suitable for communication and control, and interfacing those signals with equipment designed to perform various functions. The latter may include tele-robotics, navigation of vehicles including motorized wheelchairs, those involving "virtual reality", and those related to 3D computer graphics (e.g., visualization and exploration of imaginary or unattainable spaces).

It is known that eye movements are accompanied by the appearance of electric signals. The electric signals generated by movements of the eyes both the horizontal and vertical directions can be measured by electrodes. This method is known as electro-oculography (EOG) or alternatively electro-nystagmography (ENG). It is used in clinical medicine for studying eye movements (See, e.g., Bahill, A. T., *Bioengineering, Medical and Clinical Engineering,* Prentice-Hall, Inc., Englewood Cliffs, N.J., 1981; Neuman, M. R., Flemming, D. G., Cheung, P. W. and Ko, W. H., *Physical Sensors for Biomedical Applications,* CRC Press, Inc., Boca Raton, Fla., 1977; and Young, L. R. and Sheena, D., "Survey of Eye Movement Recording Methods", *Behavior Research Methods & Instrumentation,* 7, 5 (1975), 397–429.)

EOG is based on electrical measurement of the potential difference between the cornea and the retina which is about 1 mv (millivolt) under normal circumstances. This corneo-retinal potential creates an electrical field in the front of the head which changes in orientation as the eyeballs rotate. The resultant electrical changes can be detected by electrodes placed near the eyes. In clinical practice, the detected voltage changes are amplified and used to drive a plotting device, whereby a tracing related to eye movement is obtained. As a measure of eye position, these signals are inaccurate and noisy and therefore the EOG method has not been used for implementing eye position tracking.

Other methods of eye tracking are known. [See, e.g., Bahill, A. T., *Bioengineering, Medical and Clinical Engineering,* Prentice-Hall, Inc., Englewood Cliffs, N.J., 1981; Neuman, M. R., Flemming, D. G., Cheung, P. W. and Ko, W. H., *Physical Sensors for Biomedical Applications,* CRC Press, Inc., Boca Raton, Fla., 1977; Yamada, M., Fukuda, T. and Hirota, M., "A New Eye Movement Analyzer: Auto Calibration and Wireless Transmission", *IEEE Medical an Biological Society 11th Annual International Conference,* 1989, 861–863; and Young, L. R. and Sheena, D., "Survey of Eye Movement Recording Methods", *Behavior Research Methods & Instrumentation,* 7, 5 (1975), 397–429.]. One implementation of eye tracking, utilizes so-called reflectance methods. Reflectance methods are basically divided into two variants or subclasses. Limbus tracking involves illuminating the eye with an infra-red light emitting diode and obtaining video images of eye movement. The differential reflectance method which use laser-based eye tracking. These methods are very accurate, but also very expensive. Since many applications, e.g. those involving the handicapped, have limited markets, the issue of affordability can be crucial, putting these expensive systems out of the reach of many potential users. A further disadvantage of reflectance systems is that their detectors can obstruct the view of the user.

It is accordingly an object of the invention to provide methods and equipment which can utilize the relatively inexpensive derivation of EOG signals to provide communication and control functions, thereby permitting the design and marketing of systems affordable to various classes of users.

Another object of the present invention is to provide a system where signals associated with eye movements can be detected without obstructing the view or the field of vision of the user.

Another object of the present invention is to provide apparatus and method for efficiently using eye movement to communicate two and three dimensional location information to a machine.

Still another object of the present invention is to provide a system and method for keeping track of the direction of point of fixation and gaze of a human user and using this information in conjunction with "eye gesture, e.g., blinks, to derive commands to be carried out by an underlying application.

A further object of the present invention is to provide a system and method which utilizes eye movement to generate signals enabling interaction in virtual space.

A still further object of the present invention is to provide a system and method of provide 3D location data from coarsely quantized eye position and velocity measurements.

A still further object of the present invention is to provide a system and method which enables a user to perform selection tasks by generating command signals through the use of eye movements.

A further object of the present invention is to provide a system and method for providing commands derived from eye movements which are customized to meet individual application requirements.

SUMMARY OF THE INVENTION

Briefly and generally the invention comprises a system and method enabling humans to communicate or dialogue with each other or with external devices using EOG signals generated by eye movement and other eye "gestures". One aspect of the invention comprises a portable EOG transducer fitted to the user and a signal processor for extracting command signals from the transducer output for use in controlling task-performing functions.

GENERAL FEATURES

The system according to the present invention includes an electro-oculographic (EOG) device which relies upon the fact that the eye has characteristics similar to a battery with the cornea acting as the positive pole and the retina acting as the negative pole.

The electric signal generated by movements of the eye can be measured in both the horizontal and vertical directions by making contact measurements near the eyes. The orientation of the electric associated with the eye changes in conjunction with eye movement. This electrical change can be detected by placing electrodes near the eyes. As each of the eyes move, the voltage detected by the associated electrodes varies in accordance with that motion.

The analog electrical signal is then analyzed by a processor to derive positional information. The processing relies on published psychophysical data on human eye movement patterns. The system then correlates the positions of the eyes with spatial coordinates.

In addition to position information, the system also obtains velocity information for developing more versatile and accurate processing.

The system automatically disengages when it senses non-interaction episodes, e.g., turning to look at someone who enters the room. The system then allows re-engagement when the user generates the appropriate commands.

The user begins operation by first commencing a calibration step. During calibration, the user's eye movement pattern is analyzed as he or she visually tracks simple generated movement patterns provided on a display. Alternatively, the system may be calibrated by the user by looking at pre-defined reference points in the environment. The calibration parameters make it possible to create a smooth trajectory from the coarse data and provide appropriate visual feedback to the user. Further advantages of the calibration is further explained hereinafter.

THE DRAWINGS

Serving to illustrate exemplary embodiments of the invention are the drawings of which:

BACKGROUND AND DESCRIPTION OF THE EMBODIMENTS

Figure 1:
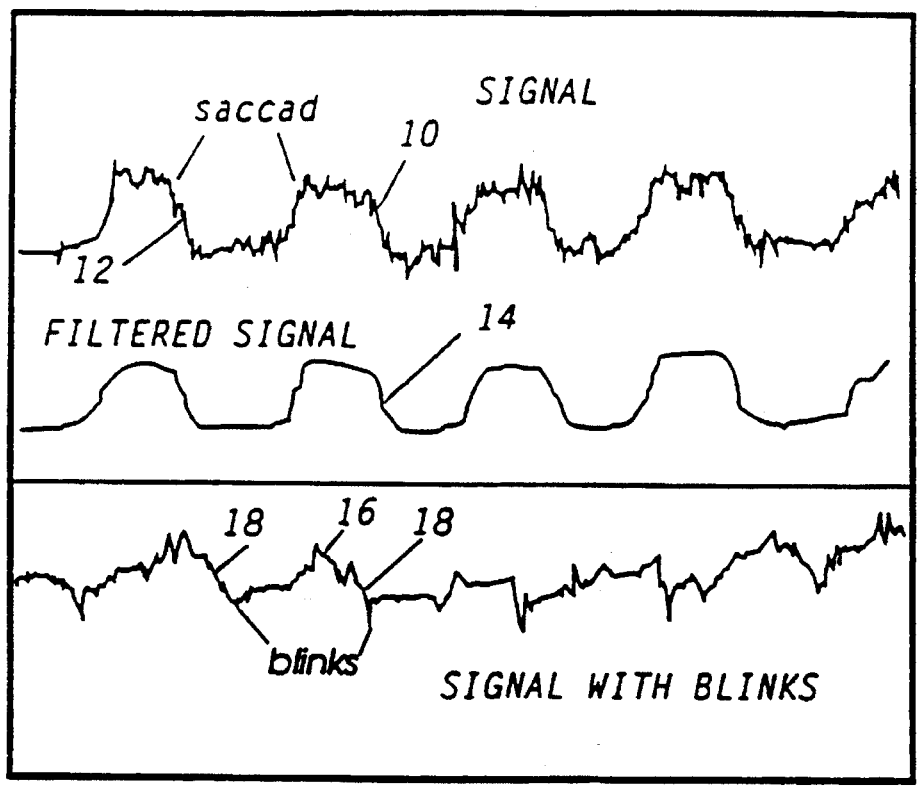
FIG. 1 illustrates an example of the signal produced by various kinds of eye movements.

Human eyes need to move in order to keep the image of interest at the central part of the retina (called the fovea). Thus the act of "taking in" a visual scene consists of fixating (moving the fovea to image) all the objects in the scene of interest. Human ocular movement has been widely studied in neurophysiology and psychology. [See, e.g., Robinson, D. A., Gordon, J. L. and Gordon, S. E., "A Model of Smooth Pursuit Eye Movement System", *Biology Cybern.,* 55, (1986), 43–57; Wall III, C. and Black, F. O., "Algorithms for the Clinical Analysis of Nystagmus Eye Movements", *IEEE Transactions on Biomedical Engineering,* 28, (September, 1981), 638–645; and Zeevi, Y. Y. and Peli, E., "Smooth Eye-Movement Control with Secondary Visual Feedback", *Journal of the Optical Society of America, A, Optics and Image Science,* 1, (June, 1984), 628–634].

These studies indicate that there are four types of eye movements, called vestibular, optokinetic, saccadic, and pursuit. The first two have to do with the largely involuntary reflex, serving to stabilize the retinal image in the presence of voluntary or involuntary head motion. The saccadic movement is used to "jump" from one object of interest to another. This is the fastest type of eye movement. The pursuit movement is used to maintain fixation on a moving object.

If the orientation of the eyes is measured, it is possible to locate the 3D position of a fixated target object by triangulation. The accuracy of the location determination depends on the accuracy with which the eye orientation is determined.

In EOG, a quantitative estimate of positional accuracy can be based on the observation that there is a change in potential of about 1 micro volt for every degree of change in eye orientation in either direction, [see, e.g., Young, L. R. and Sheena, D., "Survey of Eye Movement Recording Methods", *Behavior Research Methods & Instrumentation,* 7, 5 (1975), 397–429]. The accuracy and resolution of position calculations responsive to these eye movements are determined by the sophistication of the electronic circuitry (and hence also its cost) utilized to amplify and condition this signal.

In principle, 3D location can be determined with respect to a "head" frame of reference. In order to then determine 3D location with respect to a static environmental frame, the system would also have to measure head movement and incorporate it in the calculations.

The EOG technique does not measure head movement directly. However, using the EOG signal it is possible to estimate the distance of the fixated point from the head of the user. For example, this enables the system to determine that the user is fixating at a point outside an object of interest such as a computer display.

The signal quality of the EOG output data has been well documented in text books of neurophysiology as well as in manuals of Electro-nystagmography (ENG), the study of eye movements [see e.g., Bahill, A. T., Brokenbrough, A. E. and Troost, B. T., "Variability and Development of a Normative Database for Saccadic Eye Movements", *Invest. Opthalmol. Vis. Sci.,* 21, (1981), 116–125; Barnes, G. R., "A Procedure for the Analysis of Nystagmus and Other Eye Movements", *Aviation Space Environm. Med.,* 53 (1982) 676–682; Cohen, A., *Biomedical Signal Processing,* CRC Press, Inc., Boca Raton, Fla., 1986; Inchingolo, P. and Spanio, M., "On the Identification and Analysis of Saccadic Eye Movements—A Quantitative Study of the Processing Procedures", *IEEE Transactions on Biomedical Engineering,* BME-32, 683–694 (September 1985); and Yamada, M. and Fukuda, T., "Quantitative Evaluation of Eye Movements as Judged by Sight-Line Displacements", *SMPTE Journal,* 95, (December, 1986), 1230–1241].

The signal processing steps described herein serve to condition the data so it can be reliably interpreted. Some of the noise patterns such as the 60 Hz line frequency are removed using a notch filter. Other noise artifacts are mostly transients caused, for example, by the operation of an electrical switch in the vicinity of the electrodes, contraction of the facial or neck muscles, slippage of the electrodes due to sweat, and eye blinking.

Involuntary eye blinking is considered noise in EOG. However, the signals produced by eye blinks are, in fact, quite regular. This makes it easy to recognize and eliminate them. On the other hand, because this type of signal is quite distinct from the usual data associated with pursuit or saccadic movements, it can be recognized and categorized as such and exploited for control and communication purposes. In other words, the EOG technique can recognize and utilize eye "gestures" such as winking, blinking or a combination thereof. An example of the signal produced by various kinds of eye movements is shown in FIG. 1.

The signal 10 shown in FIG. 1 may be derived from signals detected during the movement of the eyes. As shown, slope 12 indicates that a saccadic movement has occurred.

Signal 14 illustrates the same signal 10 after it has been filtered while signal 16 illustrates the effect of blinking as indicated by slopes 18.

Figure 2A:
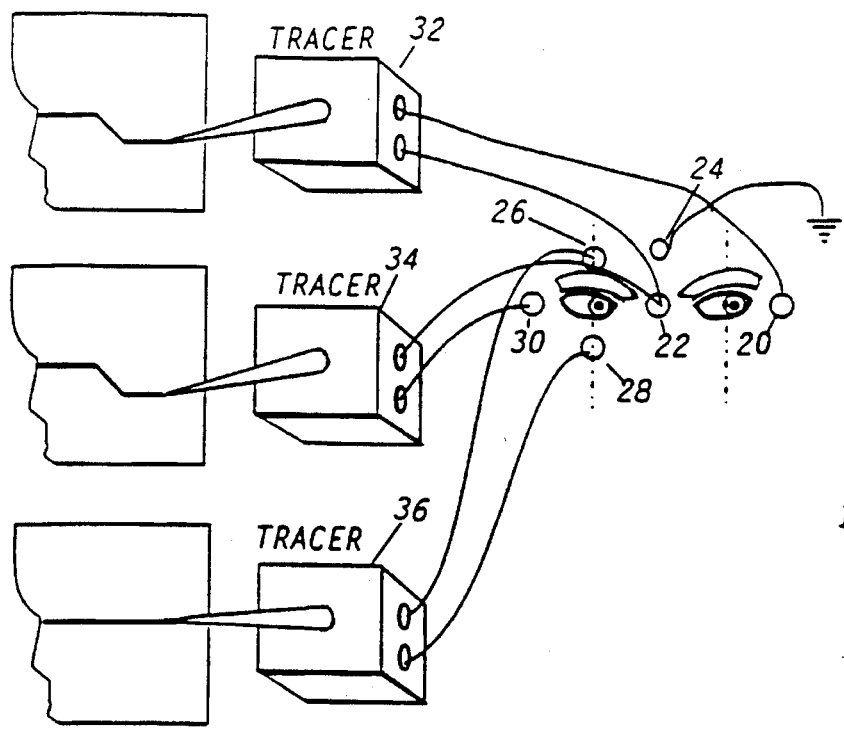
FIGS. 2A–2C illustrate signals derived by an electro-oculograph.
Figure 2C:
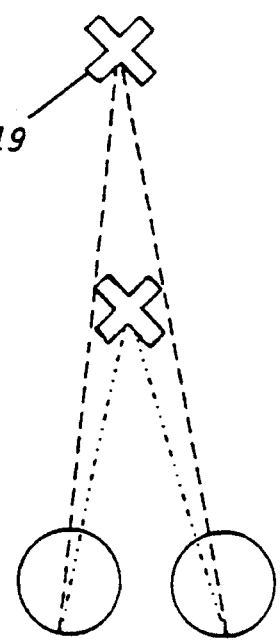
Figure 2B:
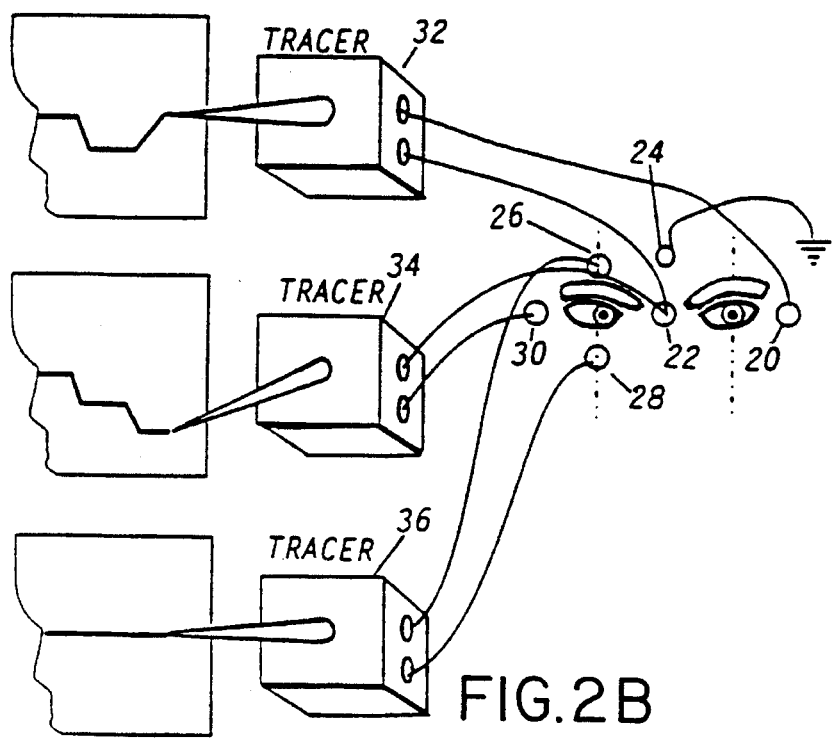

FIGS. 2A–2C illustrate how signals are derived. Electrodes 20–30 are placed around the eye region. Electrodes 20, 22 and 30 are placed along the horizontal axis of the eye for measuring left and right movement. Electrodes 20 and 22 provide signals in one channel which ultimately drive a tracer 32 for measuring horizontal movement of the LEFT eye. Similarly, electrodes 30 and 22 provide signals in a second channel to actuate a tracer 34 for measuring horizontal movements of the RIGHT eye.

Electrodes 26 and 28 placed vertically above and below the eye measure vertical movements of the right eye. These electrodes provide signals in a third channel which operates tracer 36 for measuring vertical movement of both eyes.

For many applications one vertical channel is sufficient since the eyes move up and down concurrently. Hence, a three channel system may be formed for measuring left and right movements of each eye and vertical movements of both eyes. As shown by the movement of fixated object 19 in FIG. 2c, the eyes rotate horizontally in opposite directions as distance to the object changes. This enables distance determinations.

Additional channels may be formed by placing electrodes in other locations affected by the movement of the eyes. For example, a fourth channel may be used for measuring the vertical movements of each eye separately. This permits the system to distinguish left and right blinks. As object 19 moves forward and backward each eye traces its movement generating different voltages in each channel as illustrated in FIG. 2.

Figure 5:
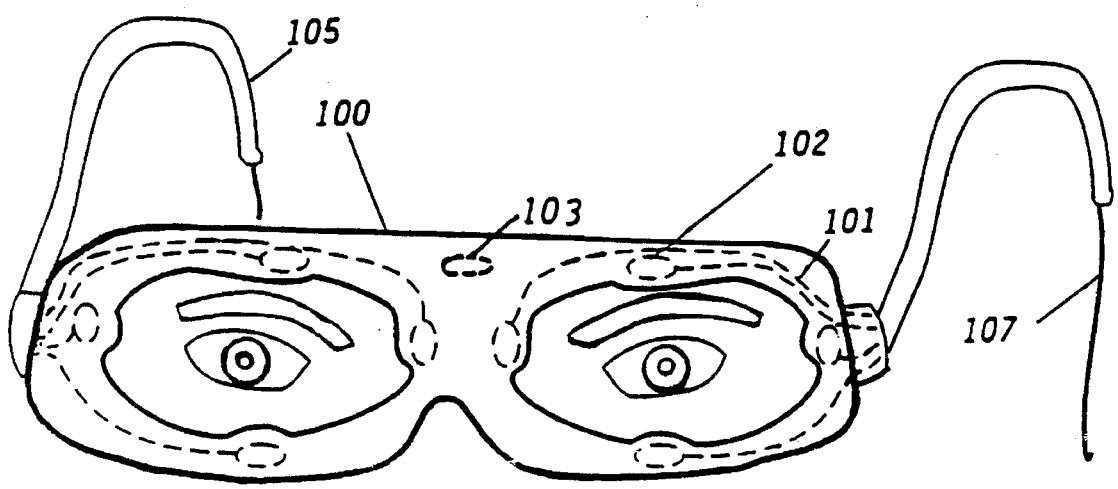
FIG. 5 illustrates one configuration for electrodes according to the invention.

FIG. 5 illustrates another possible configuration for electrodes. In this case, the electrodes 102 are disposed on an eyeglass frame or goggle 100 in appropriate locations and the electrode wires 101 are through a passage in the frame, thence through the ear attachments 105 to cables 107 which connect to the system amplifiers. Electrode 103 functions as a ground reference. The use of the goggle is easier than placing electrodes individually on the face.

To measure the EOG signals, two types of electrodes are used. One type uses small 6 mm gold-plated disks with electrical contact ensured by use of electrode cream. The other electrodes may be the type used in EKG or polygraph testing. These electrodes come with adhesive and conductive gel around an embedded conductor which makes contact with the skin.

As mentioned before, one electrode provides the reference ground necessary for proper signal measurement. This electrode may be either attached to the earlobe with a small gold-plated clip or to the arm with a strap or on the forehead.

In order to measure EOG signals, it is necessary to attach electrodes in a manner that reduces signal drift and increases ease of use.

In another embodiment of the present invention, gold-plated electrodes embedded in plastic disks and mounted on a standard audio headphone assembly are used. This "Head-Phone" holds the electrodes against the skin on the temples about the eyes with enough pressure to make contact and stay in place. This arrangement when used in conjunction with the ear clip ground is easy to apply and allows the user to move about. Means are required however to minimize drift tendencies. For this purpose, the system provides automatic zeroing with an adaptive circuit which is described in a following section.

In an alternate method, the gold electrodes are taped to the skin on either side of the eyes with standard first-aid tape. This arrangement works best when not attached close to the corners of the eyes. The use of taped-on electrodes is a useful alternative, because they are most often used by professional Ophthalmologists in a clinical setting and produce a lower to moderate amount of drift when used to derive eye movement information.

Figure 3:
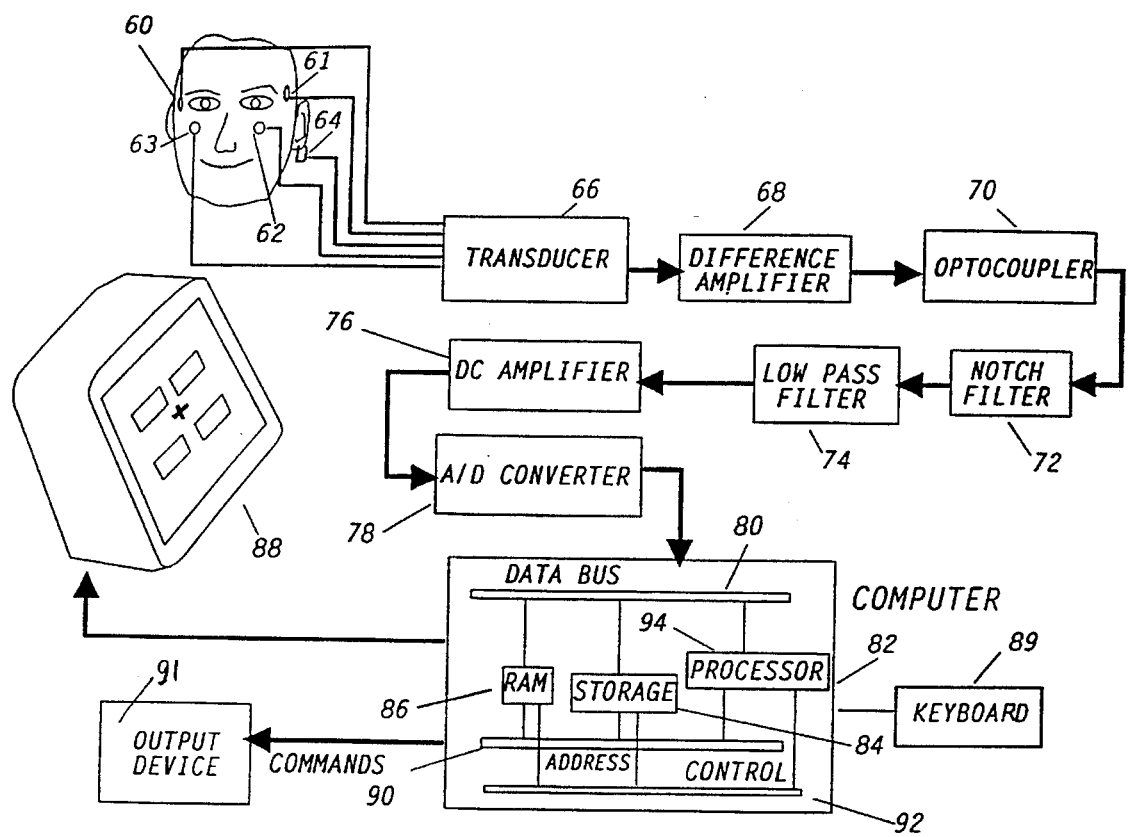
FIG. 3 illustrates block diagram of the system according to the invention.

FIG. 3 illustrates aspects of the system organization. As mentioned above, it is possible to obtain independent measurements from the two eyes. This gives rise to the four channel recording system shown in FIG. 3. Electrodes 60, 61, 62, 63 and 64 are positioned to pickup the signals fed to the four channels of the transducer. Electrode 64 is connected to an earlobe representing the reference ground.

The voltage across the electrodes 62 and 63, placed respectively a little below each eye, is indicative of the vertical orientation of each eye separately.

Similarly, electrodes 60 and 61, placed horizontally across the eyes, can measure the horizontal orientation of each eye.

As the eyes move, the voltage registered by the electrodes varies in accordance with the motion. These voltages are fed to the transducer 66 and thence to difference amplifier 68 which serves to amplify the voltages picked up by the electrodes and to supply them, via an optocoupler 70, to a notch filter 72. The latter attenuates 60 $H_z$ interference.

The filtered output of the notch filter is supplied to a 120 Hz low-pass filter 74 which removes high frequency noise. The resultant signal is then amplified in a DC amplifier 76, converted to digital form in an A to D converter 78, and inputted to the data bus 80 of a computer 82 for further processing by the computer's software. Preferably, all the additional signal processing occurs in the computer. Further, A/D converter 78 may form a part of the computer which also includes processor 94, hard disk storage 84, a complement of RAM memory 86, a monitor 88, and a keyboard 89 for setup. It may also include a floppy disk and communication ports.

In one embodiment of the present invention the signals collected for processing can include those that initiate or precede eye movements. These signals are associated with eye movements, and are generated prior to the actual movement of the eyes.

The behavior of the system is derived from software algorithms that operate on the digitized eye movement signals. Using the computer monitor 88 and a suitable environment such as an X window/UNIX arrangement, the system interacts with the user to generate, process and interpret the signals received from the electrodes as the user reacts to the display.

In order to keep the actual add-on hardware (i.e., in addition to the computing hardware) as simple as possible, it is preferred that most of the filtering and noise removal be carried out by the computer.

The data extracted from the processed EOG signals are supplied to a graphical user interface embodied in the computer's software. The user interface provides command signals to output device 91 for control and communication. In one embodiment of the invention, the data supplied to the interface are utilized in interactive feedback modes.

Figure 4:
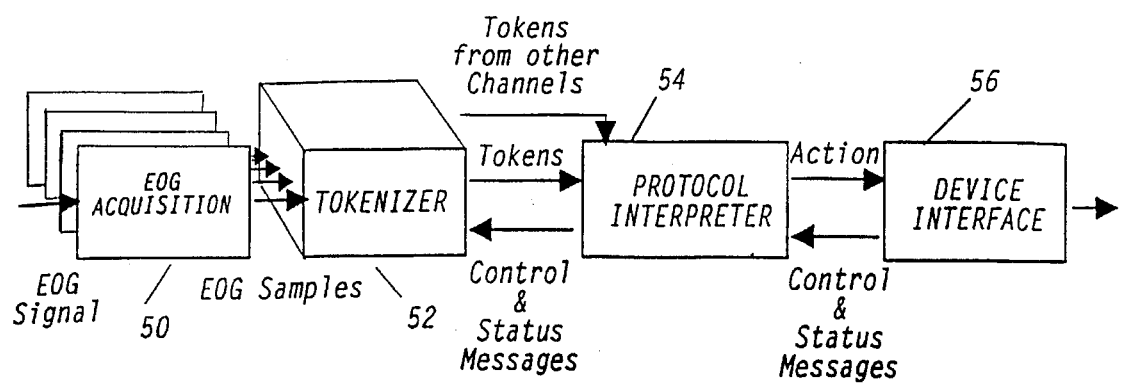
FIG. 4 illustrates one example of the system according to the invention.

FIG. 4 illustrates one example of the system processing according to the present invention. The EOG signals for each channel are picked up by the EOG acquisition stage 50 and converted to digital signals. A tokenizer 52 is coupled to the acquisition stage 50 and derives serial tokens from the EOG signals. A token is a set of signals or numbers that represents eye movements both symbolically and numerically. For example, the system may include symbolic tokens corresponding to: left eye blinking; one of the eyes moving left; eyes looking steadily at a point; eyes moving fast to the right; double blinking; one of the eyes moving right; and looking up and down. Other movements may also serve as tokens depending upon the needs of a particular application. Examples of numeric values are displacement, speed, and duration.

A protocol interpreter 54 is coupled to the tokenizer for receiving and interpreting the tokens. It may also receive tokens from other channels. When the system is initialized for a particular application or user, a protocol is accessed for interpreting various tokens. It generates various actions according to each token received. For example, as part of the protocol two blinks may mean disengage. Therefore, whenever tokens representing two blinks are generated, the protocol interpreter provides signals via an interface 56 to disengage the operation being performed. As shown in FIG. 4, control and status messages are fed back from each module to the previous module. Except for the acquisition stage 50 which is a hardware item, the above functions may be performed in hardware or by software.

Figure 6:
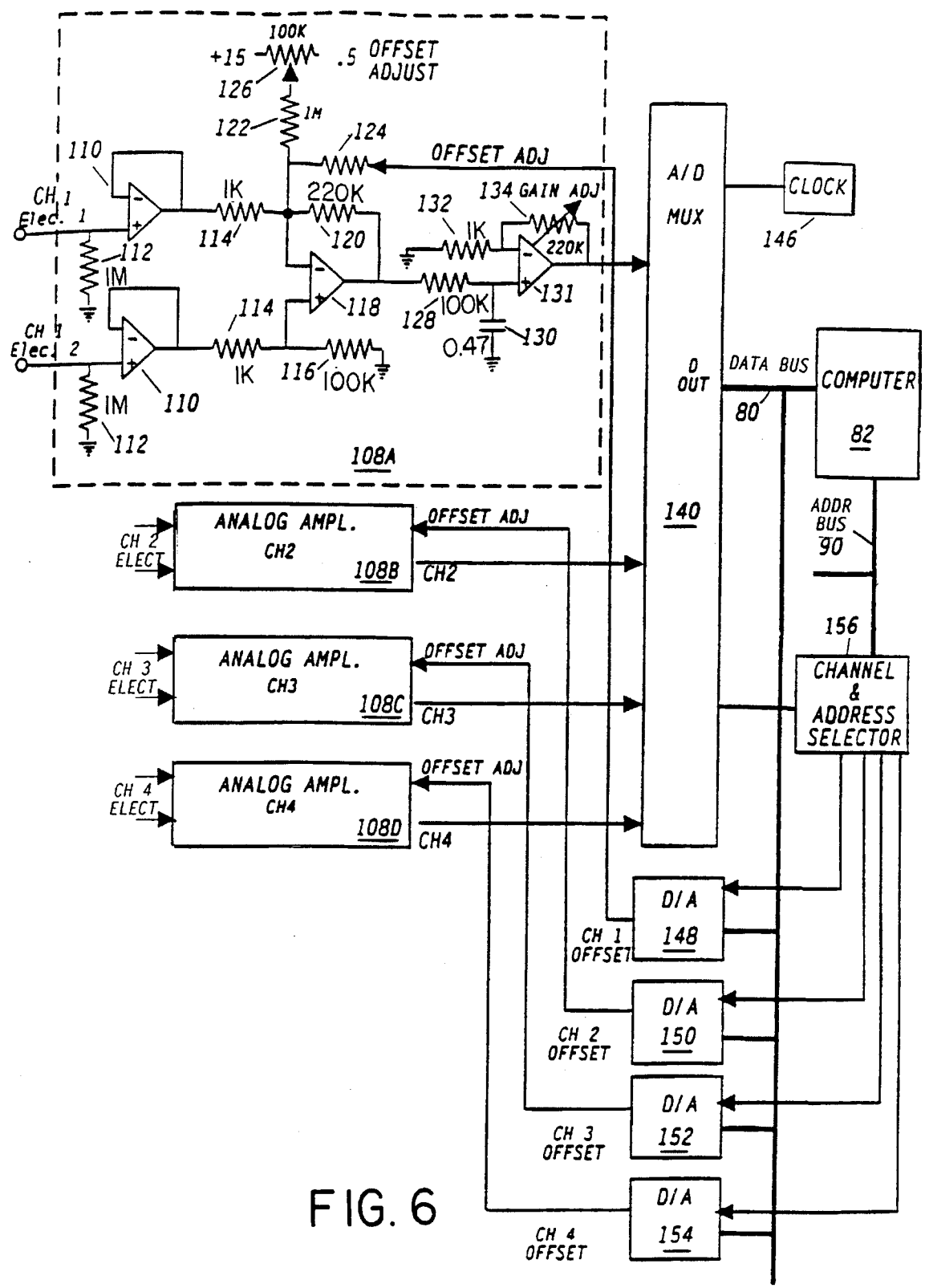
FIG. 6 illustrates block diagram of data acquisition stage of an embodiment according to the present invention.

FIG. 6 illustrates additional system details. Each channel illustrated in FIG. 6 includes signals derived from two electrodes for signal pick-up, one electrode disposed at a location near the eye, and the other electrode being connected to ground, e.g., the ear-lobe. The signal derived from the pair of electrodes for each channel is coupled to analog amplifier 108 for signal measurement. The first and second electrodes of channel 4 are coupled to analog amplifier 108A. The first and second electrodes of channels 2, 3 and 4 are similarly connected to analog amplifiers 108B, 108C and 108D, respectively.

Each analog amplifier 108 includes a first pair of buffers 110 coupled to the pair of electrodes. The outputs of the buffers are coupled to a differential amplifier circuit which includes an operational amplifier 118. The non-inverting input of operational amplifier 118 is coupled via resistance 114 to the output of buffer 110 and via a resistance 116 to ground. The inverting input of the operational amplifier is connected via resistance 114 to the output of its buffer and also to a resistive network 122 and 126, the latter providing offset adjustment. The input also receives an offset adjusting voltage via resistance 124.

The output of the operational amplifier is also fed back to its inverting input via resistor 120.

The output of the operational amplifier 118 is coupled to an active filter which includes an operational amplifier 131, feedback resistor networks 134 and 132, and capacitor 130.

During the operation of the system the signals derived from the electrodes begin to drift to the point of driving the operational amplifiers into saturation. To minimize the drift, resistor 124 is coupled to a variable voltage source, explained below, for controlling the drift that occurs during signal measurement. The drift is due to a variety of reasons. For example, after a period of time, when the electrodes are connected to the skin, the effect of perspiration or temperature rise can cause drift which can drive the operational amplifiers into saturation. By varying the voltage across resistor 124 it is possible to maintain the operational amplifier 118 in its linear region and hence offset drift occurrences.

The signals detected in channels 1–4 by analog amplifiers 108A–108D are fed into an analog to digital (A/D) converter and multiplexer 140. The digital sample corresponding to each channel is then transmitted to the computer 82 over data bus 80.

Also connected to the data bus are digital-to-analog (D/A) converters 148, 150, 152 and 154. Each (D/A) converter provides the offset adjustment voltages to each differential amplifier via its resistance 124.

Computer 82 also provides data for address selection via address bus 90. Address bus 90 is connected to channel and address selector 156. The output of the channel and address selector is coupled to the enable ports of A/D converter 140 and the D/A converters 148, 150, 152 and 154.

The channel and address selector receives addressing data via address bus 90 and decodes the addressing data to develop appropriate enable signals which are transmitted to the D/A convertors and the A/D convertor.

When the A/D multiplexer 140 is selected, a digital value corresponding to a channel sample voltage is sent to the computer via data bus 80. Conversely, if anyone of the D/A converters is selected, digital data on bus 80, is transmitted to the selected D/A convertor, converted to the equivalent analog signal and sent to the appropriate analog amplifier.

A clock 146 is coupled to A/D multiplexer 140. It sets the desired sampling rate. For a typical eye-tracking application a sampling rate of 100 samples per second for each channel is sufficient. Hence, signals detected by the analog amplifier stage in each channel are multiplexed to the A/D multiplexer and the corresponding digital samples are derived and fed to computer 82.

In order to avoid drift occurrences and ensure that the operational amplifiers are operating in their linear regions, the processor 94 (see FIG. 3) measures the detected samples and calculates their average. The processor then determines if there is any drift in the average over a period of time. If so, and in order to adjust for the drift, the processor generates an appropriate offset digital signal which is fed to the appropriate D/A converter 148, 150, 152 or 153, where it is converted to analog form and sent to the respective channel. The automatic drift control according to the present invention allows for accurate calculations of the position signals corresponding to the movement of the eyes.

The D/A and A/D hardware illustrated in FIG. 6 may be designed to fit in an expansion slot of computer 82 and be addressable.

Figure 7:
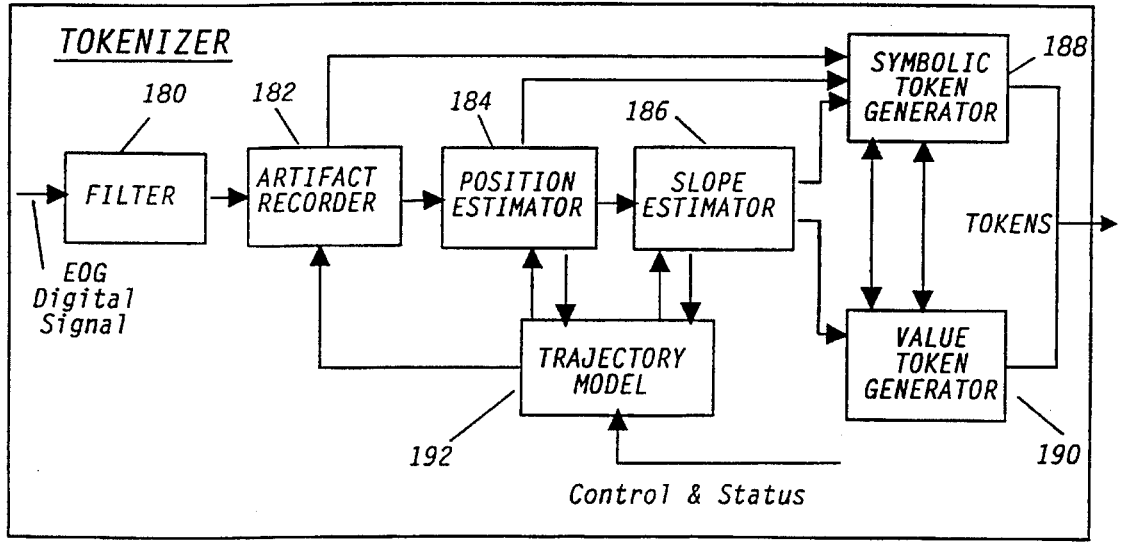
FIG. 7 illustrates the functions of signal processing according to one embodiment of the present invention.

FIG. 7 illustrates the functions of the tokenizer 52 of FIG. 4 in more detail. As mentioned before, each channel has a tokenizer for processing the EOG signal derived from the electrodes. It will be appreciated by those skilled in the art that the tokenizer can be configured both in hardware or software.

The input to the tokenizer, a digital sample corresponding to the derived EOG signal, is fed to a Gaussian filter 180. The output of the Gaussian filter is coupled to an Artifact recorder 182. The Artifact recorder also receives input from a Trajectory Model 192, enabling the artifact recorder to coarsely measure sharp slopes associated with blinking or winking motions. The Artifact Recorder also measures the duration of the blink or wink and deletes the sample(s) corresponding to associated sharp change in signal amplitude. The output of the Artifact Recorder is therefore a comparatively smooth signal corresponding to actual motions of the eyes without the effects of blinking or winking.

The output of the Artifact Recorder is coupled to a Position Estimator 184. The Position Estimator is also coupled to the Trajectory Model for estimating the actual position of the eye. The output of the Position Estimator is coupled to a Slope Estimator 186. The slope estimator is also coupled to the trajectory model for estimating the rate of change of eye displacement as reflected in the slope of the signal.

The information derived from the Artifact Recorder, the Position Estimator and the Slope Estimator, are then fed to Symbolic Token Generator 188. A Value Token Generator 190 receives input from the Position Estimator (not shown in FIG. 7), Slope Estimator and from the Symbolic Token Generator. As mentioned before, the tokens are values that represent eye movements both symbolically and numerically.

The Tokenizer first classifies the eye movement signal using parameters determined by a calibration test; it defines a token for each classification. Thereafter, during the actual eye movement measurements, the tokenizer assigns the corresponding value or token to the signal derived from eye movement, when that signal falls within the range of classification parameters defining a token and determined at least in part by the calibration test.

In order to generate appropriate tokens, the tokenizer first filters transient noise from the digital sample of the EOG signal by filter 180. The process by which this is done can be termed contextual filtering. Such filtering draws upon the literature of signal processing and digital filtering techniques [see, e.g. Ballard, D. H. and Brown, C. M., *Computer Vision*, Prentice-Hall, Englewood Cliffs, N.J., 1982; Cohen, A., *Biomedical Signal Processing*, CRC Press, Inc., Boca Raton, Fla., 1986; and Juhola, M., Jantti, V., Pyykko, I., Magnusson, M., Schalen, L. and Akesson, M., "Direction of Saccadic Eye Movements Using a Nonrecursive Adaptive Digital Filter", *Computer Meth. Programming Biomedical*, 21, (1985), 81–88]. It ensures that once a pattern of movement has been established, transient deviations from the pattern will be ignored. In contrast to more expensive commercial systems, the preferred system employs software thus minimizing the electronic signal processing hardware.

The Artifact Recorder receives another input from the Trajectory Mode 192. The Trajectory Model continuously predicts the value of the next sample based on a statistical prediction technique. In one embodiment of the present invention, the Trajectory Model predicts the value of incoming data based on a straight line extrapolation. Therefore, if the value of the current data sample is not the same as the one predicted by the Trajectory Model, the average of the sample and the predicted data is taken and substituted for the received data. The Trajectory Model may emplody other prediction techniques.

Further, if there is an abrupt change in the signal amplitude for a substantial period of time, the Trajectory Model generates a signal indicating the abrupt change. Upon receiving this indication, the Artifact Recorder realizes that a blink or a wink has occurred and consequently sends a signal to token generators 188 and 190. The Symbolic Token Generator 188 generates a value or token representing the blink or the wink; Value Token Generator 190 generates a token representing its duration. The tokens may be index numbers representing the eye gesture. Typically winking signals are generated when eyes are involuntary closed periodically; they therefore have a relatively short duration. Deliberate blinking signals are generated when eyes are voluntarily closed, for instance in generating a desired action, and therefore have a longer duration.

As noted above, the Trajectory Model 192 continuously predicts the expected value of the incoming position data. It sends the estimated value to the Position Estimator based on a straight line extrapolation method. The Position Estimator and the Trajectory Model in conjunction continuously smooth out aberrations in the signal. The Position Estimator then sends the position data to Token Generator 188 and to the Slope Estimator 186.

The Slope Estimator is also coupled to the Trajectory Model which continuously predicts the expected value of the incoming slope data, and send the estimated value to the slope estimator based on a straight line extrapolation method. The slope estimator and the trajectory model in conjunction continuously smoothen out aberrations in signal reading. The Slope Estimator then sends the slope data to token generators 188 and 190. The token generators generate appropriate tokens corresponding to slope classifications determined during the calibration stage and appropriate value information. Slope tokens can represent "static" condition, i.e. zero velocity; a "slow" state representing small velocity or a pursuit; and a "fast" condition representing saccade or fast velocity.

Figure 8A:
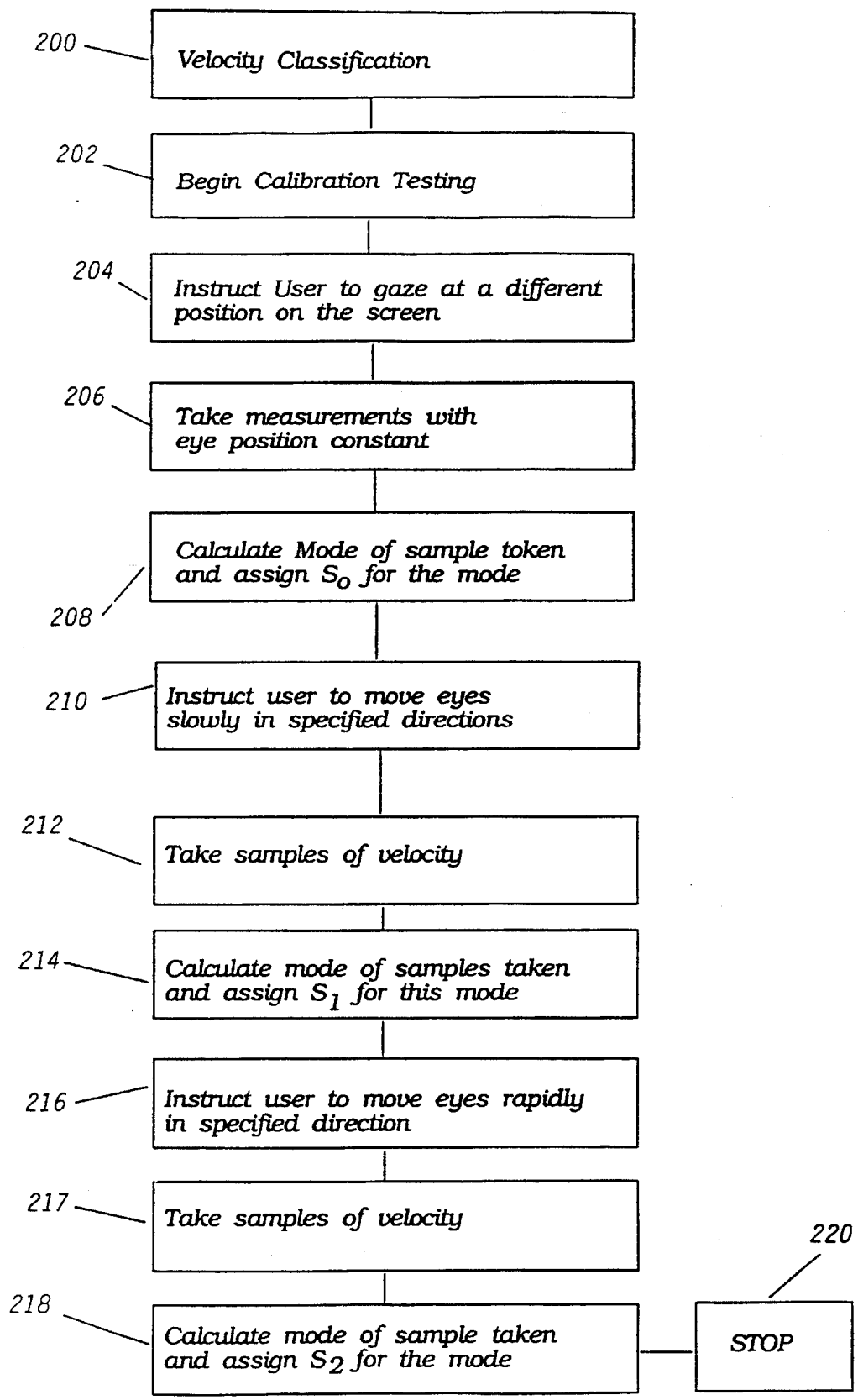
FIGS. 8A and 8B illustrate an example of the steps taken for token generation for different velocities according to one embodiment of the invention.
Figure 8B:
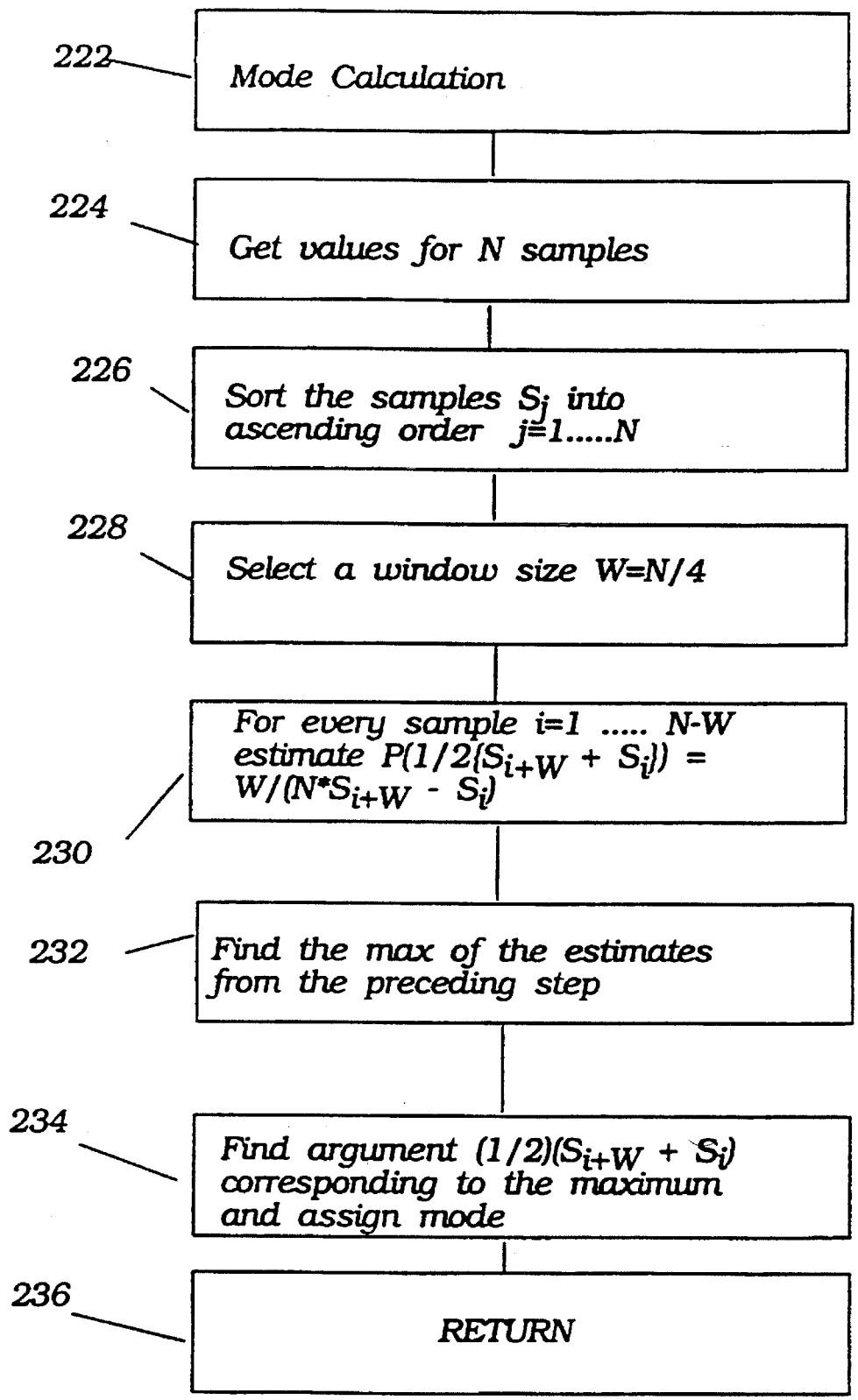

FIGS. 8A and 8B illustrate an example of the steps taken for token generation for different velocities. According to one embodiment of the present invention, three classes of slopes are defined as follows:

I. static (zero velocity)

II. slow (small velocity or pursuit)

III. fast (saccade or fast velocity)

At step 200 the velocity classification begins. At step 202 the system begins a calibration procedure. During calibration, at step 204, the user is instructed to fix the eye at different positions for a specified period of time so that the gaze is directed at different points in the visual field. At step 206, for each eye position, the system collects data corresponding to the eye positions.

At step 208 the system then calculates the modes of the position distributions and assigns the mode value $S_0$ as the first classification.

Thereafter at step 210, the system instructs the user to move his or her eyes slowly in different directions. At step 212, for each direction of movement, the system collects data corresponding to those eye movements. At step 214, the system then calculates the mode of the slow movement distribution and assigns the mode value $S_1$ as the second classification.

Thereafter at step 216, the system instructs the user to move his or her eyes rapidly in different directions. At step 217, for each direction, the system collects data corresponding to those eye movements. At step 218, the system then calculates the mode of the rapid movement distribution and assigns the mode value $S_2$ as the third classification. A token may be assigned to each one of the classifications.

FIG. 8B illustrates the steps taken to estimate the mode of collected samples. At step 222, the system begins mode estimation. At step 224 the system collects N samples of data. At step 226, the samples are sorted in an ascending order. Thereafter at step 228 the system selects the window size W where $W=N/4$.

At step 230 for every $i=1 \ldots N-W$ the system estimates $p(S)$ wherein $p(\frac{1}{2}[S_{(i+W)}+S_i])=W/(N*(S_{(i+W)}-S_i))$.

At step 232 the largest of the probability values calculated at step 230 is determined. Thereafter at step 234 the argument ½[$S_{i+w}+S_i$] corresponding to the maximum probability value is found and assigned as the mode.

The standard deviation of the above estimation for probability is sigma[p(½[$S_{(i+w)}-S_i$])]=sqrt(w)/(N*($S_{(i+w)}-S_i$)). A more rigorous mode estimation process estimates mode for different window sizes W. It then uses a maximum likelihood estimator to pick the mode among the different mode candidates obtained by the different windows S.

At run time, when the system is estimating actual eye positions and velocity, an unknown slope S is classified as I, II, or III according to |S-$S_0$|, |S-$S_1$|, or |S-$S_2$|. Thus the minimum difference decides membership and an appropriate token is assigned to the estimated velocity.

It will be appreciated by those skilled in the art that other classification rules may apply for other movements and symbolic and value tokens assigned accordingly.

In one embodiment according to the invention, calibration is measured as the ratio of actual distance measured in degrees to eye movements measured in number of detectable lefts or rights. Therefore, after every data point is processed a left, right, or no movement is returned. Any data point examined during a left will return a left and so on.

Figures 9A, 9B:
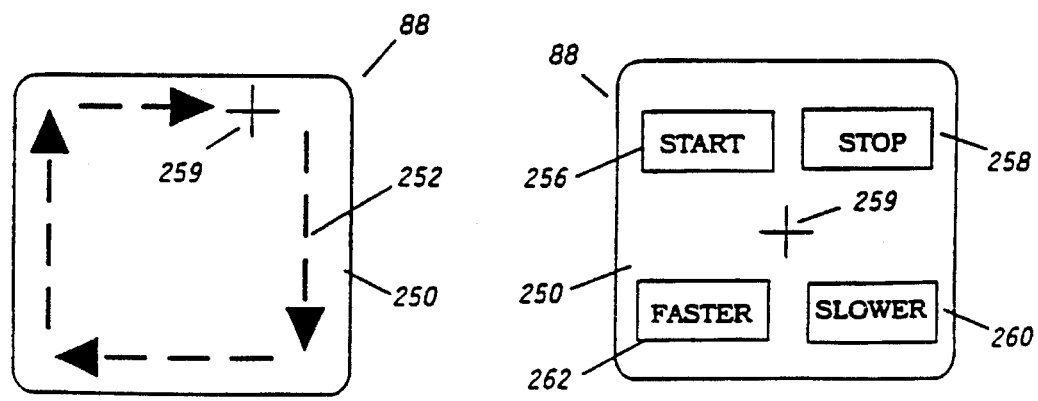
FIGS. 9A and 9B illustrate the situation where a display screen is use for calibration an interaction according to one embodiment of the invention.

FIGS. 9A and 9B illustrate the situation where a display screen 250 of monitor 88 is used for calibration and interaction. In this event the calibration is measured as the ratio of actual distance measured in pixels to eye movements measured in number of detectable lefts or rights. Preferably the user assumes a constant distance from the display. The user can set a sensitivity value manually by selecting a "comfortable" value. For example, the user may instruct the system to move the cursor a certain amount of pixels for every detectable eye movement. Alternatively, the system is calibrated by asking the user to trace with his eyes the movement 252 of cursor 259 which could illustratively span approximately 10,000 pixels, while the number of detectable eye movements are being recorded. In the latter situation calibration value is set to the amount of movement expected divided by the number of detected rights and lefts during the sampling period.

Using this method, the calibration for one type and speed of eye movements cannot be used for different eye movements. In this embodiment of the invention, when describing calibration an activity is to be calibrated in terms of angular motion of the eyes.

As the user follows the cursor along the path 252, the user's eye movements are analyzed in the computer 82 (see FIG. 3), to verify that the pattern of movement and the cursor motion is the same. This enables the calibration algorithm to calculate the idiosyncratic signal parameters associated with each particular user, for instance, the amount of voltage fluctuation in the signal corresponding to the left most and right most eye position, the velocity for smooth pursuit motion, and so on. This calibration establishes signal parameter ranges that are used in later classification and in symbolic token extraction from the signal as mentioned above.

The calibration procedures can also assist in minimizing drift. As noted above, eye voltages tend to slowly drift throughout some range. The magnitude of drift can be approximated by having the user keep his eyes fixed for an extended period while measuring changes in slope. The average slope may be used to adjust for drift.

FIG. 9b illustrates the next interaction mode which is the command mode. During command mode, the cursor 254 is moved by the system in response to and to track the user's gaze. In the exemplary interface screen of FIG. 9b, four command "buttons" are displayed: 256 for "start", 258 for "stop", 260 for "slower" and 262 for "fast". The cursor 259 is initially at the center of the display. It can be appreciated that this command generating system could control the speed of a machine by eye movement. Thus, when the user looks at the START button the cursor follows his or her gaze and moves to that button. Then the START command is activated by a prolonged gaze or by the user winking twice, causing the machine to be started. The user can consequently communicate control commands to the computer by guiding the cursor to the appropriate button and making an actuating gesture (e.g., eye blinking or winking).

In another embodiment of the invention the monitor 88 may display various objects. The user may provide predefined eye gestures to interact with the objects. For example, in a video game application the objects may be characters that can be moved to various locations on the display by providing appropriate eye gestures.

From the point of view of reliability, the coarser the quantization or classification that can be worked with, the more robust can the measurement process become. For instance, if only qualitative data or tokens are required for the three spatial axes (i.e., left/right, up/down and front/back) then the measurement is very reliable. Therefore, in static environments where the objects to be picked are fixed, symbolic tokens alone can be adequate when combined with properly designed interaction protocols that utilize knowledge of the structure of the environment to make sense of the qualitative input data.

The problem with using the eyes as a pointing device is that humans also use their eyes for other purposes. Thus during the interaction episode the user might blink naturally, turn his or her head to look at someone or something else, or quickly dart a glance away and then back to the screen. The system is programmed to recognize such irrelevant signals and discard them. Natural blinks cause low voltage blips that do not occur in rapid succession. On the other hand, valid blinks for registration of commands must be vigorous and in rapid succession, and thus can be distinguished from natural blinks.

An alternative technique is to require single eye blinking for transmitting commands. This too can be used to distinguish from natural eye blinks.

Since eye signals from both eyes is measured, a rough estimate of the distance of the fixated point from the center of the forehead may be obtained using the protocol interpreter. Therefore, each channel provides a value token corresponding to the position of each eye separately. The protocol interpreter may process the value tokens by triangulation techniques to estimate the distance. When the head is turned away from the screen, the system will be able to detect the abrupt motion, because the fixated distance changes from the "norm" recorded during calibration. This causes the system to disengage and freeze the cursor on the screen. To re-engage the user performs the gesture of fixating on the cursor and winking twice. Other measurable gestures may also be used.

When the user looks away from the screen by performing a saccade, the system recognizes the irrelevancy of the motion by comparing it with the classification range of velocities calculated during calibration. Again, this causes the system to disengage.

The illustrative system communicates location interactively without independent head position measurements. This lack of information is substantially overcome by the calibration step before actual interaction. It is assumed that during an interaction "episode," the user's head will not move appreciably.

In another embodiment of the invention, head movements may be measured by analyzing EOG signals. More accurate head movements measurements may be implemented by adding additional electrodes to detect actual head movements.

To achieve the foregoing functions the system includes interface control algorithms to control cursor motion and decision algorithms to drive the overall interface system. The user interface for graphical applications employs tools for interactive prototyping of 2D and 3D user interfaces [see, e.g., Giacalone, A. and Kaufman, A., "Tools for Interactive Prototyping of 2D and 3D User Interfaces", in *Augmented Interactive Computer Capabilities,* A. Klinger, (ed.), Plenum Press, 1990] and within the already developed framework of the Cube 3D user interface described in Kaufman, A., "A Three-Dimensional User Interface", *NCGA '89 Tenth Annual Conference,* Philadelphia, Pa., April 1989, 361–367; Kaufman, A. and Yagel, R., "Towards a Three-Dimensional User Interface", in *Augmented Interactive Computer Capabilities,* A. Klinger, (ed.), Pelnum Publishing, 1990; Kaufman, A., Yagel, R. and Bakalash, R., "Direct Interaction with a 3D Volumetric Environment", *Proceedings 1990 Symposium on Interactive 3D Graphics,* Snowbird, Utah, March 1990, 33–34; and Kaufman, A. and Yagel, R., "Tools for Three-Dimensional User Interfaces", in *Work with Computers: Organizational, Management, Stress and Health Aspects,* M. J. Smith and G. Salvendy, (eds.), Elsevier Science Publishers B.V., Amsterdam, The Netherlands, September 1989, 468–475].

3D APPLICATIONS

The above described techniques can record the stereo disparity between the eyes so that depth information can be recovered. This enables the system to follow the movement of the 3D point of fixation (i.e., the point that the eye is fixating upon) and measure its 3D velocity. This characteristic facilitates use for remote navigation and control applications of the type stated above and permits the operator to exercise navigational control of machinery using gaze directed control in three space. The system employs tokens generated from the input channels 1–4 of FIG. 3, to measure position and velocity of the point of fixation or gaze point. The protocol interpreter 54 of FIG. 4 enables interaction using somewhat rough spatial position and velocity input from the eye gaze measurement device.

The 3D system provides approximate location of eye fixation. After suitable calibration to allow for individual variances, it provides data about the gaze point in 3D as well as the time rate of change (i.e., velocity) of this point. This data is somewhat coarse. Therefore, the system embodies rules for interaction between the operator and the machine to overcome the limitations of the information channel. These rules of interaction or protocol, allow reliable and unambiguous communication between human and machine, communication between two or more people at the same time. Furthermore, it is possible to store the eye-movements during an interaction episode and allow the user to follow the same movements upon retrieval to the stored data.

Another embodiment of the present invention may be applied to wheelchair navigation by a physically challenged human operator. In a typical application it is required to control the direction of motion of the wheelchair and its speed. In addition, the operator should be free to look around and observe points of interest in the scene. This means that certain deliberate eye gesture patterns (or signatures) should convey distinct commands to the machine. Furthermore, unconscious or natural eye movement patterns should not be interpreted as wheelchair control commands. The eye movement pattern provides a serial information stream. To meet these conditions the protocol recognizes certain predefined tokens in the stream as previously described.

Based on the information stream obtained from the 2D system the signal analysis algorithms are designed to detect certain simple patterns or tokens. It is desirable for the operator to define his or her own distinctive gestures or tokens according to personal preference or convenience, and to use those "signs" to indicate various control commands. Thus, for example, one would fixate at an environmental point for two seconds or more and then wink twice to cause the wheelchair to move in the direction of that point. Someone else might prefer some other sequence of actions, e.g., when the disability does not permit winking. For this reason there is incorporated in the Protocol Interpreter a rule-based pattern learning component to enhance flexibility and reliability.

Another application according to one embodiment of the present invention is eye tracking and control while the user is looking through a microscope or a binocular. Since EOG measurements do not obstruct the eye, it is possible to extend such eye tracking movements to microscopic or binocular applications. Accordingly, during calibration for the microscopic use, a calibration plate is first placed for the user's view. The user is then instructed to provide the eye movements or gestures for generating parameter classifications. During the interaction mode, the actual movements are detected and corresponding tokens are generated for the protocol interpreter to provide appropriate actions to the particular interface.

Calibration for binocular use can similarly be accomplished by providing a marked lens on the binocular for deriving eye movement or gestures and generating parameter classifications. Another method for calibrating for binocular use may be employed when a marked lens is not available. In this case, the user is first instructed to calibrate eye movements and gestures with the naked eye. The optical characteristics of the binocular is then provided to the system. The processor then transforms naked eye calibration parameters by incorporating optical characteristics into the field of vision with binoculars.

The invention in its broader aspects therefore is not limited to the specific embodiment herein shown and described but departures may be made therefrom within the scope of the accompanying claims without departing from the principles of the invention and without sacrificing its chief advantages.

We claim:

1. A method for determining the 3D position of a gaze point comprising the steps of:

detecting signals associated with eye position from each eye;

processing said detected signals from each eye to determine the gaze point in 3D; and determining whether the 3D gaze point is located at a point outside of a presentation area.

2. The method of claim 1, further comprising the step of measuring head movement and determining the 3D location of said gaze point with respect to a static environmental frame.

3. The method of claim 1 wherein said detected signals are EOG signals.

4. The method of claim 1, where said presentation area is a display screen.

5. A method for determining the 3D position of a gaze point comprising the steps of:

detecting signals associated with eye position from each eye;

processing said detected signals from each eye to determine and store a normative fixated distance for a user's gaze at an object;

further processing said detected signals from each eye and determining when the 3D gaze point of said user is located at a point outside said normative fixated distance of said object; and initiating a command signal in response to said determination.

6. The method of claim 5, where said object is a display screen.

7. The method of claim 6, where said command signal causes a computer program to disengage and freeze a cursor on said display screen.

8. The method of claim 5, where said detected signals are EOG signals.

* * * * *